United States Patent
Colvin, Jr. et al.

(10) Patent No.: US 7,135,342 B2
(45) Date of Patent: Nov. 14, 2006

(54) ELECTRO-OPTICAL SENSING DEVICE WITH REFERENCE CHANNEL

(75) Inventors: Arthur E. Colvin, Jr., Mt. Airy, MD (US); Robert W. Lynn, Silver Spring, MD (US)

(73) Assignee: Sensors for Medicine and Science, Inc., Germantown, MD (US)

( * ) Notice: Subject to any disclaimer, the term of this patent is extended or adjusted under 35 U.S.C. 154(b) by 695 days.

(21) Appl. No.: 10/137,329

(22) Filed: May 3, 2002

(65) Prior Publication Data

US 2002/0164813 A1    Nov. 7, 2002

Related U.S. Application Data

(60) Provisional application No. 60/288,498, filed on May 4, 2001.

(51) Int. Cl.
*G01N 21/00* (2006.01)

(52) U.S. Cl. .................... 436/164; 422/82.05

(58) Field of Classification Search ............ 422/82.05, 422/82.07, 82.08, 82.11; 436/68, 95, 164, 436/165, 169, 170, 172
See application file for complete search history.

(56) References Cited

U.S. PATENT DOCUMENTS

| | | | |
|---|---|---|---|
| 3,229,684 A | 1/1966 | Nagumo et al. | |
| 3,399,667 A | 9/1968 | Nishimoto et al. | |
| 3,576,554 A | 4/1971 | Temps, Jr. et al. | |
| 3,612,866 A | 10/1971 | Stevens | |
| 3,649,833 A | 3/1972 | Leaf | |
| 3,800,300 A | 3/1974 | Van Oosterhout | |
| 3,839,708 A | 10/1974 | Bredesen et al. | |
| 3,853,117 A | 12/1974 | Murr | |
| 3,872,455 A | 3/1975 | Fuller et al. | |
| 3,893,111 A | 7/1975 | Cotter | |
| 3,949,388 A | 4/1976 | Fuller | |
| 3,972,320 A | 8/1976 | Kalman | |
| 4,041,954 A | 8/1977 | Ohara | |
| 4,160,971 A | 7/1979 | Jones et al. | |
| 4,186,749 A | 2/1980 | Fryer | |

(Continued)

FOREIGN PATENT DOCUMENTS

DE    4341903 A1    6/1995

(Continued)

OTHER PUBLICATIONS

Search Report in Corresponding PCT application, no date.

(Continued)

*Primary Examiner*—Jill Warden
(74) *Attorney, Agent, or Firm*—Rothwell, Figg, Ernst & Manbeck (57) ABSTRACT

An electro-optical sensing device for detecting the presence and concentration of an analyte in a liquid or gaseous medium includes a pair of indicator elements positioned to receive radiation from a radiation source and transmit radiation to a pair of photosensitive elements. The indicator elements each contain indicator molecules having an optical characteristic responsive to the presence of an analyte; however, one of the indicator elements is covered by an analyte-impermeable chamber that renders the indicator element insensitive to the presence of the analyte in the medium outside the chamber so that it can be used as a reference to cancel environmental and systemic variables that affect both indicator elements. The chamber preferably holds an analyte-containing fluid in contact with the reference indicator element so that the indicator elements operate under nominally identical conditions. The indicator element used to measure the analyte in the external medium is preferably also covered, but in a manner that provides direct contact between the analyte and the indicator element.

13 Claims, 5 Drawing Sheets

U.S. PATENT DOCUMENTS

| | | | |
|---|---|---|---|
| 4,262,632 A | 4/1981 | Hanton et al. |
| 4,361,153 A | 11/1982 | Slocum et al. |
| 4,401,122 A | 8/1983 | Clark, Jr. |
| 4,531,526 A | 7/1985 | Genest |
| 4,580,059 A | 4/1986 | Wolfbeis et al. |
| 4,617,277 A | 10/1986 | Bohl |
| 4,632,807 A | 12/1986 | Marsoner |
| 4,677,008 A | 6/1987 | Webb |
| 4,680,268 A | 7/1987 | Clark, Jr. |
| 4,703,756 A | 11/1987 | Gough et al. |
| 4,704,029 A | 11/1987 | Van Heuvelen |
| 4,730,188 A | 3/1988 | Milheiser |
| 4,737,464 A | 4/1988 | McConnell et al. |
| 4,746,830 A | 5/1988 | Holland |
| 4,752,115 A | 6/1988 | Murray, Jr. et al. |
| 4,755,667 A | 7/1988 | Marsoner |
| 4,854,328 A | 8/1989 | Pollack |
| 4,863,470 A | 9/1989 | Carter |
| 4,875,483 A | 10/1989 | Vollmann et al. |
| 4,935,632 A | 6/1990 | Hart |
| 4,992,794 A | 2/1991 | Brouwers |
| 5,001,054 A | 3/1991 | Wagner |
| 5,010,893 A | 4/1991 | Sholder |
| 5,012,286 A | 4/1991 | Kawano et al. |
| 5,028,918 A | 7/1991 | Giles et al. |
| 5,036,869 A | 8/1991 | Inahara |
| 5,039,490 A | 8/1991 | Marsoner et al. |
| 5,041,826 A | 8/1991 | Milheiser |
| 5,084,699 A | 1/1992 | DeMichele |
| 5,095,309 A | 3/1992 | Troyk et al. |
| 5,117,825 A | 6/1992 | Grevious |
| 5,143,066 A | 9/1992 | Komives et al. |
| 5,157,262 A | 10/1992 | Marsoner et al. |
| 5,190,729 A | 3/1993 | Hauenstein et al. |
| 5,211,129 A | 5/1993 | Taylor et al. |
| 5,218,343 A | 6/1993 | Stobbe et al. |
| 5,235,326 A | 8/1993 | Beigel et al. |
| 5,244,810 A | 9/1993 | Gottlieb |
| 5,272,090 A | 12/1993 | Gavish et al. |
| 5,281,825 A | 1/1994 | Berndt et al. |
| 5,300,120 A | 4/1994 | Knapp et al. |
| 5,314,457 A | 5/1994 | Jeutter et al. |
| 5,341,805 A | 8/1994 | Stavridi et al. |
| 5,342,789 A | 8/1994 | Chick et al. |
| 5,372,133 A | 12/1994 | Hogen Esch |
| 5,462,880 A | 10/1995 | Kane et al. |
| 5,512,246 A | 4/1996 | Russell et al. |
| 5,517,313 A | 5/1996 | Colvin, Jr. |
| 5,584,870 A | 12/1996 | Single et al. |
| 5,628,310 A | 5/1997 | Rao et al. |
| 5,630,836 A | 5/1997 | Prem et al. |
| 5,633,724 A | 5/1997 | King et al. |
| 5,674,288 A | 10/1997 | Knapp et al. |
| 5,682,149 A | 10/1997 | Hofman |
| 5,704,352 A | 1/1998 | Tremblay et al. |
| 5,708,957 A | 1/1998 | Chuang et al. |
| 5,725,578 A | 3/1998 | Knapp et al. |
| 5,735,887 A | 4/1998 | Barreras, Sr. et al. |
| 5,833,603 A * | 11/1998 | Kovacs et al. ............... 600/317 |
| 5,855,609 A | 1/1999 | Knapp |
| 5,922,285 A * | 7/1999 | Melendez et al. ....... 422/82.08 |
| 5,939,609 A | 8/1999 | Knapp et al. |
| 5,963,132 A | 10/1999 | Yoakum |
| 5,966,404 A | 10/1999 | Yokota et al. |
| 5,977,431 A | 11/1999 | Knapp et al. |
| 5,995,860 A | 11/1999 | Sun et al. |
| 6,002,954 A | 12/1999 | Van Antwerp et al. |
| 6,009,878 A | 1/2000 | Weijand et al. |
| 6,011,984 A | 1/2000 | Van Antwerp et al. |
| 6,040,194 A | 3/2000 | Chick et al. |
| 6,073,050 A | 6/2000 | Griffith |
| 6,092,530 A | 7/2000 | Weissman et al. |
| 6,099,482 A | 8/2000 | Brune et al. |
| 6,113,856 A * | 9/2000 | Lawrence et al. ............ 422/58 |
| 6,141,591 A | 10/2000 | Lenarz et al. |
| 6,198,950 B1 | 3/2001 | Kraus |
| 6,212,431 B1 | 4/2001 | Hahn et al. |
| 6,259,937 B1 | 7/2001 | Schulman et al. |
| 6,268,161 B1 | 7/2001 | Han et al. |
| 6,289,229 B1 | 9/2001 | Crowley |
| 6,304,766 B1 | 10/2001 | Colvin, Jr. |
| 6,321,067 B1 | 11/2001 | Suga et al. |
| 6,330,464 B1 * | 12/2001 | Colvin et al. ................ 600/316 |
| 6,330,885 B1 | 12/2001 | Weissman et al. |
| 6,368,275 B1 | 4/2002 | Sliwa et al. |
| 6,387,048 B1 | 5/2002 | Schulman et al. |
| 6,411,108 B1 | 6/2002 | Douglas et al. |
| 6,415,186 B1 | 7/2002 | Chim et al. |
| 6,419,624 B1 | 7/2002 | Burton et al. |
| 6,424,847 B1 | 7/2002 | Mastrototaro et al. |
| 6,430,444 B1 | 8/2002 | Borza |
| 6,443,891 B1 | 9/2002 | Grevious |
| 6,447,448 B1 | 9/2002 | Ishikawa et al. |
| 6,454,710 B1 | 9/2002 | Ballerstadt et al. |
| 6,475,750 B1 | 11/2002 | Han et al. |
| 6,505,059 B1 | 1/2003 | Kollias et al. |
| 6,542,777 B1 | 4/2003 | Griffith et al. |
| 6,545,483 B1 | 4/2003 | Douglas |
| 6,564,807 B1 | 5/2003 | Schulman et al. |
| 6,585,763 B1 | 7/2003 | Keilman et al. |
| 6,614,406 B1 | 9/2003 | Amundson et al. |
| 6,666,821 B1 | 12/2003 | Keimel |
| 6,671,527 B1 | 12/2003 | Petersson et al. |
| 6,682,490 B1 | 1/2004 | Roy et al. |
| 6,694,158 B1 | 2/2004 | Polak |
| 6,711,423 B1 | 3/2004 | Colvin, Jr. |
| 6,731,961 B1 | 5/2004 | Braig et al. |
| 6,731,976 B1 | 5/2004 | Penn et al. |
| 6,772,011 B1 | 8/2004 | Dolgin |
| 6,802,811 B1 | 10/2004 | Slepian |
| 6,806,552 B1 | 10/2004 | Woo et al. |
| 6,809,507 B1 | 10/2004 | Morgan et al. |
| 6,809,653 B1 | 10/2004 | Mann et al. |
| 6,809,701 B1 | 10/2004 | Amundson et al. |
| 2002/0016535 A1 | 2/2002 | Martin et al. |
| 2002/0019707 A1 | 2/2002 | Cohen et al. |
| 2002/0032435 A1 | 3/2002 | Levin |
| 2002/0118134 A1 | 8/2002 | Chen |
| 2002/0123779 A1 | 9/2002 | Zarinetchi et al. |
| 2002/0161288 A1 | 10/2002 | Shin et al. |
| 2003/0025645 A1 | 2/2003 | Amundson et al. |
| 2003/0050542 A1 | 3/2003 | Reihl et al. |
| 2003/0098783 A1 | 5/2003 | Pagnol |
| 2003/0113934 A1 | 6/2003 | Kwon |
| 2003/0125612 A1 | 7/2003 | Fox et al. |
| 2003/0140931 A1 | 7/2003 | Zeijlemaker et al. |
| 2003/0169169 A1 | 9/2003 | Wuidart et al. |
| 2003/0172940 A1 | 9/2003 | Rogers et al. |
| 2003/0195400 A1 | 10/2003 | Glukhovsky |
| 2003/0213495 A1 | 11/2003 | Fujita et al. |
| 2004/0027306 A1 | 2/2004 | Amundson et al. |
| 2004/0048394 A1 | 3/2004 | Kirchhevel |
| 2004/0147801 A1 | 7/2004 | Kugler et al. |
| 2004/0181155 A1 | 9/2004 | Glukhovsky |
| 2004/0199059 A1 | 10/2004 | Brauker et al. |

FOREIGN PATENT DOCUMENTS

| | | |
|---|---|---|
| DE | 19615380 A1 | 3/1997 |
| DE | 19826294 C1 | 2/2000 |
| EP | 0309214 A2 | 3/1989 |
| EP | 0309214 A3 | 3/1989 |
| EP | 0597566 A1 | 5/1994 |
| EP | 0619101 A1 | 10/1994 |

| | | | |
|---|---|---|---|
| EP | 0646313 A1 | 4/1995 | |
| EP | 0693271 A1 | 1/1996 | |
| EP | 0834734 A2 | 4/1998 | |
| EP | 0834734 A3 | 4/1998 | |
| FR | 2680672 A1 | 3/1993 | |
| GB | 2258589 A | 2/1993 | |
| WO | WO 87/04900 A1 | 8/1987 | |
| WO | WO 92/07505 A1 | 5/1992 | |
| WO | WO 96/16593 A1 | 6/1996 | |
| WO | WO 96/25978 A1 | 8/1996 | |
| WO | WO 97/33513 A1 | 9/1997 | |
| WO | WO 98/52023 A1 | 11/1998 | |
| WO | WO 99/66309 A1 | 12/1999 | |
| WO | WO 00/13003 | 3/2000 | |

OTHER PUBLICATIONS

Jie Lin et al. "Sol-gel glass as a matrix for chemical biochemical sensing" *Trends in Analytical Chemistry*, 16(4):200-211 (1997).

Alan Baron et al. "Submillisecond response times of oxygen-quenched luminescent coatings" *Rev. Sci. Instrum.* 64(12):3394-3402 (1993).

Brauker et al., "Neovascularization of synthetic membranes directed by membrane microarchitecture", *Journal of Biomedical Materials Research*, vol. 29, 1517-1524 (1995).

Chuang and Arnold, "Radioluminescent Light Source for Optical Oxygen Sensors", *Analytical Chemistry*, vol. 69, No. 10, 1899-1903, 1997.

Geller, et al., "Immunoisolation of Tumor Cells: Generation of Antitumor Immunity Through Indirect Presentation of Antigen", *Journal of Immunotherapy*, 20(2):131-137 (1997).

Geller, et al., "Use of An Immunoisolation Device for Cell Transplantation and Tumor Immunotherapy", baxter Healthcare Corp., Illinois pp. 1-23 w/attached Figures 1-7 (undated).

Shamlou et al., "Amphiphilic networks. X. Diffusion of glucose and insulin (and nondiffusion of albumin) through amphiphilic membranes", *Journal of Biomedical Materials Research*, vol. 35, 157-163 (1997).

Kennedy, "Tailoring polymers for biological uses" *Chemtech*, pp. 24-32, Feb. 1994.

Tuan, "Recombinant Protein Protocols, Detection and Isolation", *Methods in Molecular Biology*, vol. 63, pp. 373-387.

Ward, "Development of a Hybrid Artificial Pancreas with a Dense Polyurethane Membrane", *ASAIO Journal*, vol. 39, No. 3, pp. M261-M267, 1993.

Wilkins, "Biomaterials for Implanted Closed Loop Insulin Delivery System: A Review", *Biosensors and Bioelectronics 5*, pp. 167-203, 1990.

Advertisement pamphlet entitled "RFID: Everything you need to know" by Motorola Indala Corparation, 1996, 1997 (5 pages).

Pamphlet entitled "Divvying up the biostent market", *BioCentury, The Bernstein Report on BioBusiness*, pp. A6, Aug. 10, 1998.

Advertising pamphlet entitled "Biocompatibility, controlled porosity, inertness, strength and comformability.", *Gore-Tex Medical Products*, 1990 (4 pages).

Product pamphlet for "Preclude Pericardial Membrane", *W.L. Gore & Associates, Inc.*, 1996 (2 pages).

Product pamphlet for "The Duraflo® Biocompatible Treatment", *Baxter Healthcare Corporation*, 1995 (4 pages).

O'Toole et al., "Laminin-5 inhibits human keratincoyte migration", *Exp Cell Res*, 233:2 330-9, 1997 (abstract only).

"Mini-Portable Reader Standard and Extended Models" Hughes Identification Devices information pamphlet HS5105L Series (4 pages).

"Implantable Transponder" Trovan Electronic Identification Systems pamphlet, Model—ID 100. (2 pages).

"Hand Held Reader" Trovan Electronic Identification Systems pamphlet, Model—LID 500. (2 pages).

Wouters et al. "A Low Power Multi-Sensor Interface for Injectable Microprocessor-Based Animal Monitoring System" *Sensors and Acutuators A*, 41-42 (1994) 198-206.

"DIOG Database Guide (Standard Search Service)" SRS Information Technologies, 1987 (7 pages).

"Injectable Transponder Small Size" Hughes Identification Devices information pamphlet TX1400L (2 pages).

* cited by examiner

PRIOR ART

FIG. 4

PRIOR ART

ELECTRO-OPTICAL SENSING DEVICE WITH REFERENCE CHANNEL

RELATED APPLICATION

This patent application claims priority of provisional patent application 60/288,498, filed May 4, 2001.

BACKGROUND OF THE INVENTION

1. Field of the Invention

The invention relates to electro-optical sensing devices for detecting the presence or concentration of an analyte in a liquid or gaseous medium. More particularly, the invention relates to an electro-optical sensing device having a signal channel responsive to the presence of an analyte in a liquid or gaseous medium and a reference channel that is not responsive to the presence of the analyte in the medium.

2. Discussion of the Background Art

U.S. Pat. No. 5,517,313, the disclosure of which is incorporated herein by reference, describes an electro-optical sensing device that detects the presence and amount of an analyte using fluorescence of an indicator molecule. Broadly speaking, in the context of the field of the present invention, indicator molecules are molecules having one or more optical characteristics affected by the local presence of an analyte. In one embodiment of the device according to U.S. Pat. No. 5,517,313, a light source is located at least partially within a layer of material containing indicator molecules that fluoresce when illuminated by the light source. Alternatively, the light source is located at least partially within a wave guide layer such that light emitted by the source strikes and causes the indicator molecules to fluoresce. A high-pass filter allows fluorescent light emitted by the indicator molecules to reach a photosensitive element while filtering out scattered light from the light source.

The fluorescence of the indicator molecules employed in the device described in U.S. Pat. No. 5,517,313 is modulated, i.e., attenuated or enhanced, by the local presence of an analyte. For example, the orange-red fluorescence of the complex tris(4,7-diphenyl-1,10-phenanthroline)ruthenium (II) perchlorate is quenched by the local presence of oxygen. Therefore, this complex can be used advantageously as the indicator molecule in an oxygen sensor. Indicator molecules whose fluorescence properties are affected by various other analytes are known as well.

In the sensing device described in U.S. Pat. No. 5,517,313, the material containing the indicator molecules is permeable to the analyte. Thus, the analyte can diffuse into the material from the surrounding test medium, thereby affecting the fluorescence of the indicator molecules. The light source, indicator molecule-containing material, high-pass filter, and photodetector are configured such that fluorescent light emitted by the indicator molecules impacts the photodetector such that an electrical signal is generated that is indicative of the concentration of the analyte in the surrounding medium.

In order to make accurate measurements based on a single variable, such as analyte concentration, the design of the sensing device must isolate the effects of analyte concentration from all other variables that may influence operation of the device. One way to do this is to measure all other influential variables using specific transducers, and assuming the relationship is well defined and predictable, compensate for these factors mathematically. Importantly, this method requires a means of measuring the influential variable specifically, and a detailed mathematical model describing and predicting its behavior over time.

Figure 1:
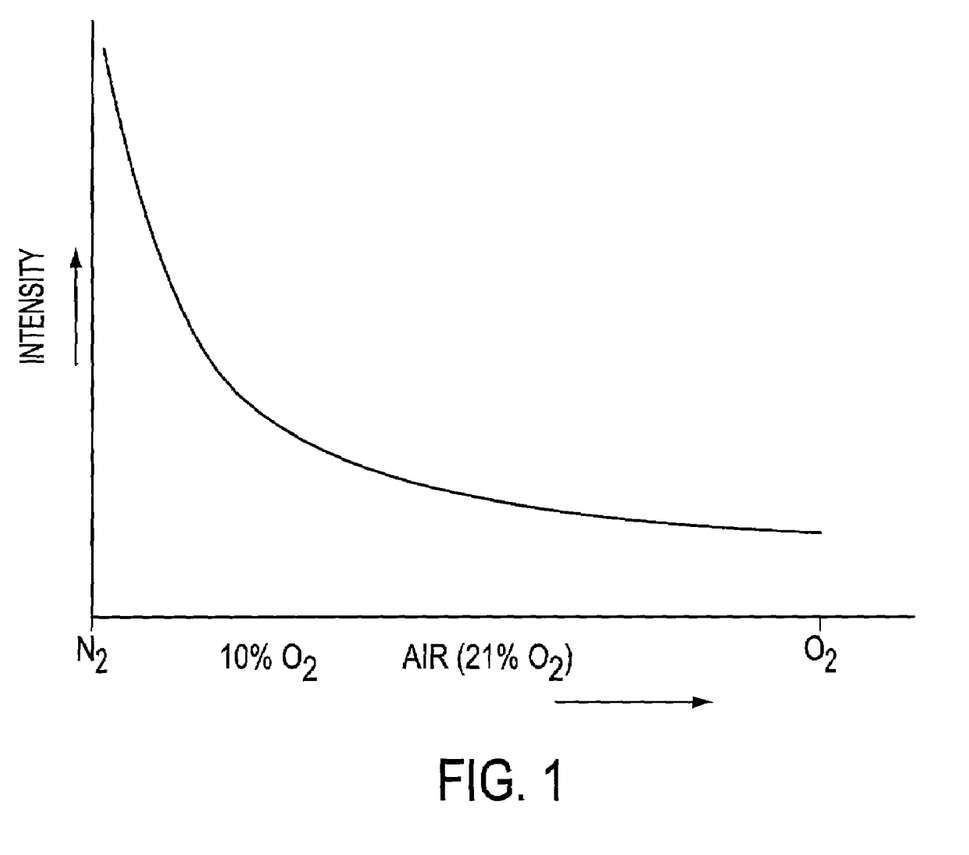
FIG. 1 is a graph illustrating the Stern-Volmer relationship between oxygen concentration and light intensity emitted by a fluorescent oxygen indicator molecule.

In the example of the indicator molecule Ruthenium tris-biphenylphenanthroline, for example, the relationship between indicator fluorescence and oxygen concentration is described by the Stern-Volmer equation:

$$I/I_O = 1 + K_{SV}[pO_2]$$

where $I/I_O$ is an intensity ratio, $pO_2$ is oxygen concentration, and $K_{SV}$ is the Stern-Volmer constant. If the output from a sensor constructed using this type of indicator were recorded from within an environment which isolated all variables except oxygen concentration, we should see a plot as shown in FIG. 1. One can employ the Stern-Volmer plot as shown to measure an intensity in the presence and absence of oxygen (the analyte) and then find the corresponding oxygen concentration from the x-axis using the plot as a calibration curve.

Figure 2:
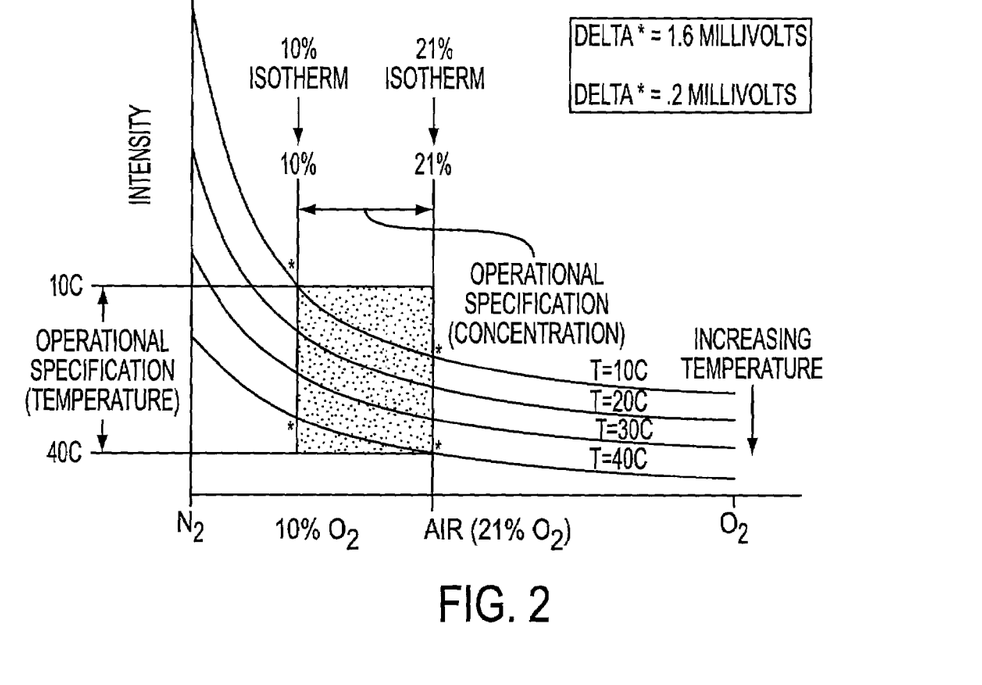
FIG. 2 is a graph illustrating the effect of temperature on the Stern-Volmer relationship.

In reality, however, $K_{SV}$ is a function of temperature, and in most practical applications, the temperature of the test medium can be expected to change substantially. The temperature can also change very rapidly. To account for the temperature sensitivity of $K_{SV}$, the Stern-Volmer relationship can be represented by a series of curves, as shown in FIG. 2, corresponding to different temperatures.

Introduction of a second variable such as temperature thus makes measurement of the first variable (i.e., analyte concentration) much more difficult. It is necessary to know the temperature accurately in order to know which of the Stern-Volmer plots to use for finding the correct oxygen concentration from a measured intensity value.

Figure 3:
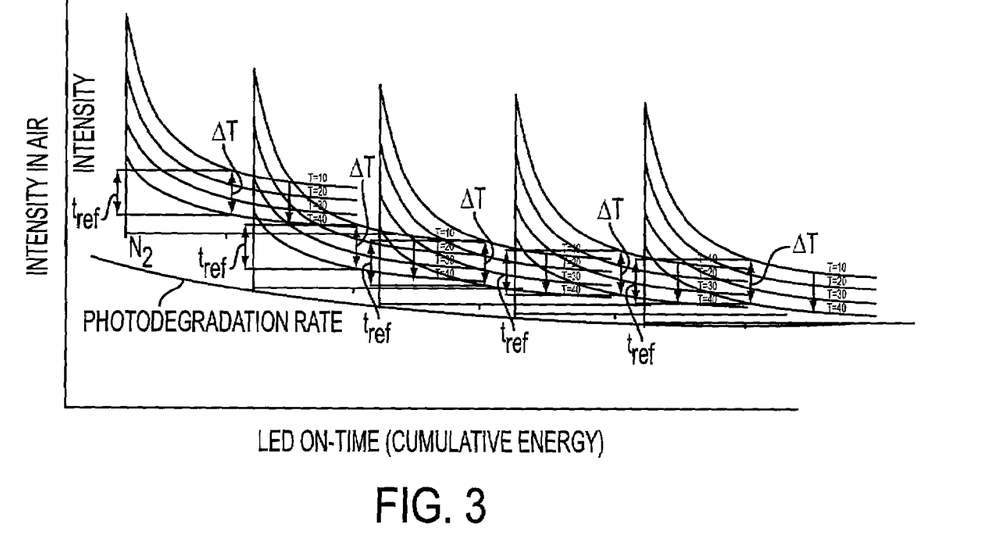
FIG. 3 is a graph illustrating the combined effects of temperature and photodegradation on the Stern-Volmer relationship over time.

An example of another influential variable is signal drift. Drift is less predictable than temperature because a multitude of known, and often, unknown, factors are causative. One of many such drift examples is illustrated by photo-oxidation in the case of the indicator Ruthenium tris-biphenylphenanthroline. Photo-oxidation, or photo-bleaching, is a well described degradation which occurs when a (typically photochemical) reaction occurs between the indicator and ambient oxygen. (In the case of the indicator Ruthenium tris-biphenylphenanthroline, the photodegradation occurs due to singlet oxygen.) This degradation reaction results in the covalent and permanent alteration of the indicator molecular structure. Once oxidized, the indicator loses it known performance characteristics and its sensitivity to the intended analyte. If a variable drift component due to photo-oxidation is superimposed over the previous temperature dependent variable shown in FIG. 2, the result is a complex plot of the type shown in FIG. 3. FIG. 3 shows what a Stern-Volmer calibration plot looks like under the influence of only three variables—changing oxygen concentration, changing temperature, and changing amplitude as a result of ongoing drift due to photo-oxidative degradation. It is not possible to know which of the plots to use for finding oxygen concentration without knowledge of the temperature and the amount of degradation experienced by the sensor.

Yet another example of error that may be introduced is from variable excitation light levels. Since the excitation light source directly "pumps" the fluorescence detected from the indicator, any fluctuation or degradation in the source light will directly be introduced as error into the calibration. Light source drift can be caused by transient changes in the sensor power supply or due to simple operational life degradation in the light source itself. Some means of correcting for this drift is necessary to making an accurate analyte measurement from sensor-supplied data.

From the above, it will be appreciated that, in order to design an electro-optical sensing device for the purpose of measuring a single analyte, some means of correcting for kinetic, molecular stability, and system influences which would otherwise introduce error into the measurement is required. These influential factors can become complex and are highly interdependent. For example, an increase in temperature will also tend to increase the rate of degradation due to photo-oxidation. There are many more known and often unknown influential factors than the three examples described. The result is a very complex and difficult to understand series of interdependent variables that directly affect the accuracy of a measurement by an electro-optical sensing device.

One method of correcting for the matrix of potential variables is to construct a reference channel that is responsive to all variables except the presence of the analyte in the external environment. The output from the reference channel may then be used to cancel the effect of such variables on the sensing channel, for example by taking the ratio of the sensing and reference channel outputs. In the absence of any change in the amount of analyte in the external environment, this ratio should remain constant over time so that, if the ratio is plotted, the result would be a flat line. This ensures that any change in the output ratio is due entirely to any change in the amount of analyte in the external environment.

Several examples of using a reference channel in this manner during analyte detection are known in the art. For example, U.S. Pat. No. 3,612,866, the entire disclosure of which is incorporated herein by reference, describes a fluorescent oxygen sensor having a reference channel containing the same indicator chemistry as the measuring channel, except that the reference channel is coated with varnish to render it impermeable to oxygen. U.S. patent application Ser. No. 09/383,148, filed Aug. 26, 1999 and entitled "Optical-Based Sensing Devices" (which issued as U.S. Pat. No. 6,330,464 on Dec. 11, 2001), the disclosure of which is incorporated herein by reference, discloses another fluorescent oxygen sensing device having a reference channel that starts out with the same base chemistry as the sensing or signal channel but is further processed to block oxygen diffusion, for example by coating the reference channel with a material that is impermeable to oxygen.

This approach, however, may induce other differences between the channels that cannot be canceled by taking the ratio of the outputs. For example, the output from the reference channel may be increased or decreased due to reflectivity of the coating material. If the gain stages for each channel are designed the same, one could be running at substantially higher levels than the other due to differences in reflectivity. In addition, ambient light that might be present in the external environment at the same wavelength as the fluorescent emission would probably not be picked-up by the reference channel and, thus, would probably not be canceled.

Yet another difference may stem from the fact that surface chemical properties of the coating create the dominant properties of the reference channel whereas the chemical properties of the indicator material or matrix create the dominant properties of the sensing channel. Susceptibility to dust and condensation, chemical compatibility, and wear, would be expected to create other differences.

It is also expected that mechanical micro-thermal influences driven by surface turbulence would be different in a reference channel that has been "blanketed" and protected. Moreover, specific absorption or diffusion characteristics may be different. The rate of photo-oxidation would be expected to be dramatically different as the light scattering or absorbing influence from the coating may intensify the excitation flux on the indicator molecule. This would result in different rates of photo-bleaching thereby removing a key benefit sought from use of the reference channel.

Importantly, the inherent solubility of the analyte within the coating material will establish the concentration as seen by the reference channel. For example, if the analyte is oxygen, the inherent solubility of the coating material for oxygen will be the oxygen level maintained at the interface between the coating material and the top surface of the reference channel. Assuming this solubility results in an equilibrium concentration much less than the concentration of oxygen in air, then the reference channel will "see" a relatively anoxic environment. It will therefore perform as if it were in an anoxic environment. If the indicator molecule were a Ru complex as mentioned above, then the fluorescence of the reference channel will be much greater than the signal channel at sensor baseline because of the inverse relationship between oxygen quenching and fluorescence intensity. Further, because there is less oxygen in equilibrium with the reference channel on average in this example, the rate of photo-oxidation (beyond the previously described light scatter influence) will be reduced by the ratio of oxygen in the coating versus oxygen in air. Any chemical reaction with alteration of, or inclusion of, the chemical components of the coating material within the indicator matrix upon initial application will alter the performance characteristics relative to the signal channel.

Figure 4:
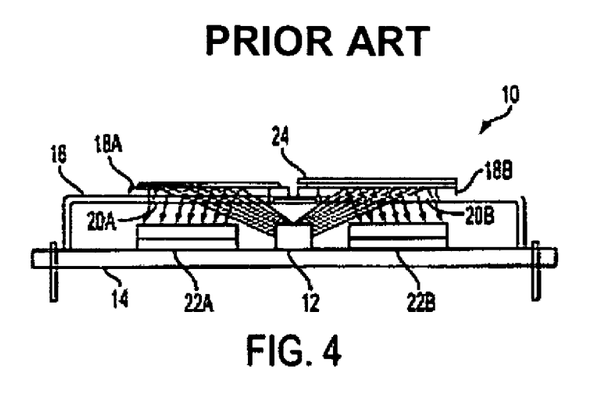
FIG. 4 is a sectional side view of a related electro-optical sensing device having an optical reference channel coated to prevent diffusion of an analyte therethrough.

FIG. 4 illustrates an optical sensing device 10 of the same general type as described in U.S. Pat. No. 6,330,464 having an excitation source 12 in the form of an LED mounted on a substrate 14 within a housing 16, a pair of indicator membranes 18A and 18B mounted over openings 20A and 20B formed in the housing, and a pair of photosensitive elements 22A and 22B on opposite sides of the LED. The indicator membranes have the same base chemistry, however, the indicator membrane shown on the right in FIG. 4 is coated with a material 24 that is impermeable to oxygen in an attempt to form a reference channel.

Figure 5:
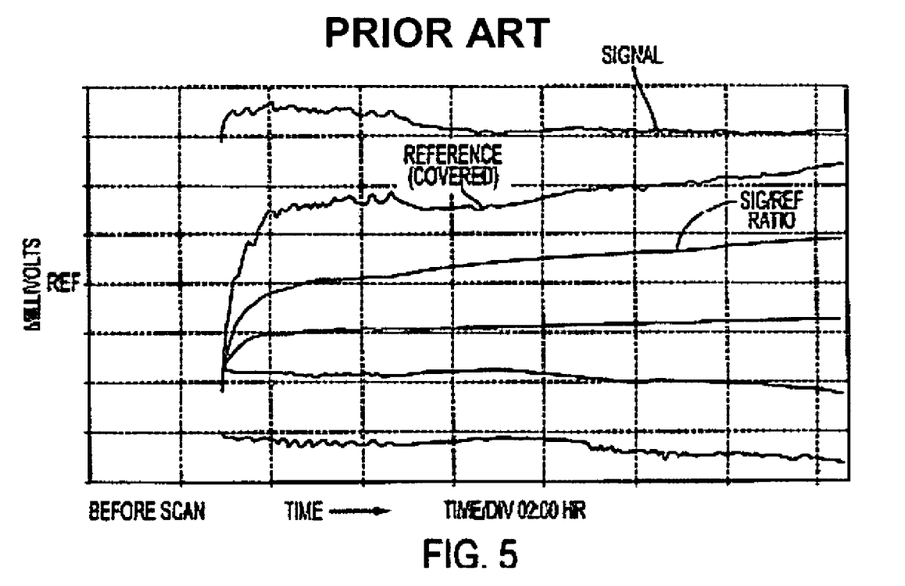
FIG. 5 is a graph demonstrating the effects of temperature and photodegradation over time for the signal and reference channels of the electro-optical sensing device shown in FIG. 4.

FIG. 5 is a graph of actual test results for a sensing device of the type shown in FIG. 4 illustrating significantly different responses for the signal and reference channels over an extended period of time during which the sensing device is exposed to ambient air having a constant oxygen concentration. It can be seen that the ratio of the signal and reference channel outputs is not a flat line as desired, but an increasing function that makes interpretation of the results complex.

In addition to the foregoing, there are other methods of using a reference during analyte detection. For example, U.S. Pat. Nos. 4,861,727 and 5,190,729, the entire disclosures of which are incorporated herein by reference, describe oxygen sensors employing two different lanthanide-based indicator chemistries that emit at two different wavelengths, a terbium-based indicator being quenched by oxygen and a europium-based indicator being largely unaffected by oxygen. U.S. Pat. No. 5,094,959, the entire disclosure of which is also incorporated herein by reference, describes an oxygen sensor in which a single indicator molecule is irradiated at a certain wavelength and the fluorescence emitted by the molecule is measured over two different emission spectra having two different sensitivities to oxygen. Specifically, the emission spectra which is less sensitive to oxygen is used as a reference to ratio the two emission intensities. U.S. Pat. Nos. 5,462,880 and 5,728,422, the entire disclosures of which are also incorporated herein by reference, describe a radiometric fluorescence oxygen sensing method employing a reference molecule that is substantially unaffected by oxygen and has a photodecomposition rate similar to the indicator molecule. Additionally, Muller, B., et al., ANALYST, Vol. 121, pp. 339–343 (March 1996), the entire disclosure of which is incorporated herein by reference, describes a fluorescence sensor for dissolved $CO_2$, in which a blue LED light source is directed through a fiber optic coupler to an indicator channel and to a separate reference photodetector which detects changes in the LED light intensity.

In addition, U.S. Pat. No. 4,580,059, the entire disclosure of which is incorporated herein by reference, describes a fluorescent-based sensor containing a reference light measuring cell for measuring changes in the intensity of the excitation light source—see, e.g., column 10, lines 1, et seq. Furthermore, U.S. Pat. No. 4,617,277, the entire disclosure of which is also incorporated herein by reference, describes an absorbance-based sensor for carbon monoxide, in which a reference element reflects light from a source to a reference photocell to determine when a measuring element needs replacement due to irreversible color change.

There remains a need in the art for an electro-optical sensing device with a reference channel that responds in essentially the same manner as the measuring channel to all environmental and systemic factors except the presence of an analyte of interest in the external environment.

SUMMARY OF THE INVENTION

A first aspect of the present invention is generally characterized in an electro-optical sensing device for detecting the presence and concentration of an analyte in an ambient fluid (i.e., liquid or gaseous medium) including a pair of indicator elements positioned to receive excitation radiation from a radiation source and to transmit resultant radiation to a pair of photosensitive elements. The indicator elements each contain indicator molecules having an optical characteristic responsive to the presence of an analyte; however, one of the indicator elements is covered by an analyte-impermeable chamber that renders the indicator element insensitive to the presence of the analyte in the external environment so that it can be used as a reference to cancel environmental and systemic variables that affect both indicator elements. The chamber preferably holds an analyte-containing fluid in contact with the reference indicator element so that the indicator elements operate under nominally identical conditions. The indicator element used to measure the analyte in the external medium is preferably also covered, but in a manner that provides direct contact between the analyte and the indicator element.

The reference can be used to compensate or correct for: changes or drift in the component operation intrinsic to the make-up of the sensing device; environment conditions external to the sensor; or combinations thereof. For example, the reference can be used to compensate or correct for internal variables induced by, among other things: aging of the radiation source; changes affecting the performance or sensitivity of the photosensitive elements; deterioration of the indicator molecules; changes in the radiation transmissivity of the indicator elements, etc. In other examples, the reference can be used to compensate or correct for environmental variables (e.g., variables influenced by factors external to the device, such as temperature), that could affect the optical characteristics or apparent optical characteristics of the indicator molecule irrespective of the presence or concentration of the analyte.

Another aspect of the present invention is generally characterized in an electro-optical sensing device including a radiation source that emits radiation; first and second photosensitive elements configured to receive radiation and output an electrical signal in response thereto; first and second indicator elements positioned to receive radiation from the radiation source and to transmit radiation to the first and second photosensitive elements, respectively, the indicator elements each containing indicator molecules with an optical characteristic responsive to the presence of an analyte; and an analyte-impermeable chamber covering at least a portion of the second indicator element so as to render the second indicator element insensitive to the presence of the analyte in a medium external to the device; whereby the ratio of output signals from the first and second photosensitive elements can be used to measure the presence and concentration of the analyte in the external medium.

The chamber of the sensing device can be filled with an analyte-containing fluid. The fluid can be a liquid (e.g., water) or a gas (e.g., air). The analyte-containing fluid can be of the same type as the external medium or of a different type. If the analyte is a gas, the partial pressure of the analyte in the chamber fluid is preferably within the range of expected partial pressures of the analyte in the surrounding medium.

An example of a suitable indicator molecule is tris(4,7-diphenyl-1,10-phenanthroline)ruthenium(II) perchlorate.

The device can include a housing mounting the first and second indicator elements, the first and second photosensitive elements, and the radiation source. An analyte-impermeable cover can be mounted on the housing to define at least a portion of the chamber covering the second indicator element. If an opening is formed in the housing, the second indicator element and the cover can be mounted on opposite sides of the opening to define the chamber therebetween. The cover can include a plug that extends into the opening. The cover can be formed of any suitable material but is preferably formed of metal. An analyte-permeable first cover can also be mounted on the housing over the first indicator element, if desired. The first cover can include a bore formed therethrough to provide fluid communication between the first optical indicator element and the external medium. First and second openings can be formed in the housing, with the first indicator element and the first analyte-permeable cover being mounted on opposite sides of the first opening, and the second indicator element and the analyte-impermeable second cover being mounted on opposite sides of the second opening to define the chamber therebetween. The first and second covers are preferably substantially similar in configuration with the exception of the bore.

Still another aspect of the present invention is generally characterized in a method of detecting an analyte in a fluid medium using an electro-optical sensing device having a first indicator element exposed to the fluid medium and a second indicator element at least partially covered by an analyte-impermeable chamber that renders the second indicator element insensitive to the presence of the analyte in the fluid medium so that it can be used as a reference to cancel environmental and systemic variables that affect both indicator elements.

Some of the advantages of the present invention over the prior art include increased accuracy, enhanced mechanical protection of the indicator elements, ease of manufacturing, and prevention of contamination including condensation.

The above and other objects, features and advantages will be further appreciated based on the following description in conjunction with the attached drawings.

BRIEF DESCRIPTION OF THE DRAWINGS

These and other objects of the invention will be apparent from the detailed description of the invention and the following figures, which are given by way of example and not limitation, and in which.

DETAILED DESCRIPTION OF THE PREFERRED EMBODIMENT

Figure 6:
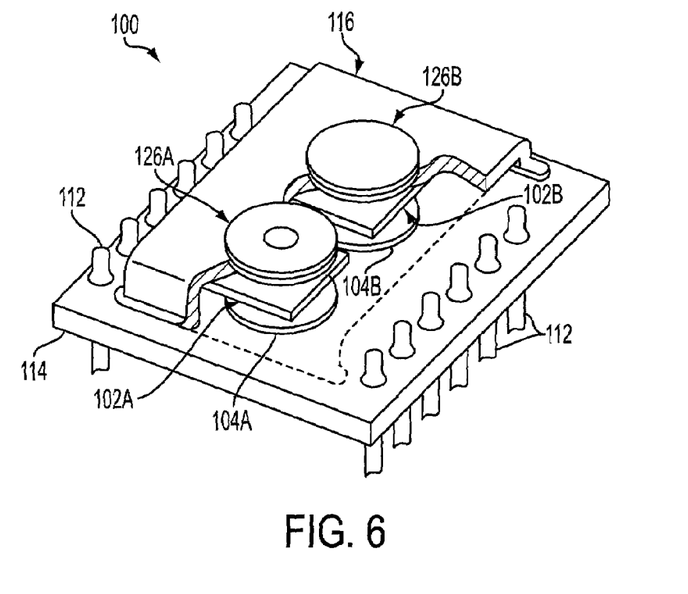
FIG. 6 is a perspective view, partly cutaway, showing an embodiment of an electro-optical sensing device according to the present invention.
Figure 7:
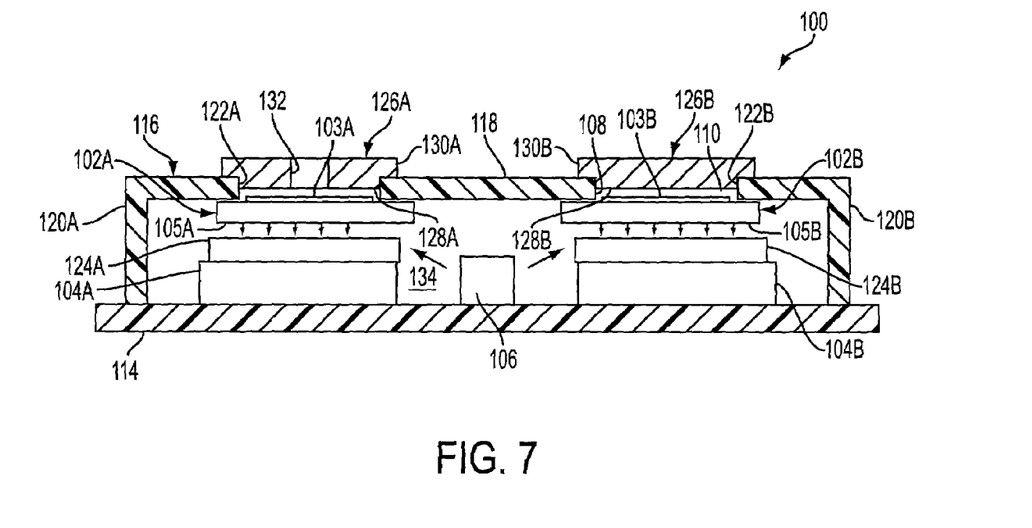
FIG. 7 is a sectional side view, taken through line 7—7 in FIG. 6, showing further details of the electro-optical sensing device.

An electro-optical sensing device 100 according to the present invention is illustrated in FIGS. 6 and 7. Sensing device 100 generally includes a signal channel with an indicator element 102A and a photosensitive element 104A, a reference channel with an indicator element 102B and a photosensitive element 104B, and a radiation source 106 providing excitation radiation for both the signal and reference channels. The indicator elements 102A and 102B each include an indicator layer or membrane containing indicator molecules having one or more optical characteristics that are affected by the local presence of an analyte. The indicator membrane 103A of the signal channel is exposed to an exterior of the device and is thus responsive to the local presence of an analyte in the external environment or medium. The indicator membrane 103B of the reference channel is covered and is thus not responsive to the local presence of an analyte in the external environment. Since the membranes are similar in all other respects, a ratio of the outputs from the signal and reference channels will cancel-out changes common to both channels, such as changes in operation intrinsic to the sensing device and/or environment changes external to the sensing device, leaving only those changes in the signal channel output due to presence of the analyte. The foregoing aspects of the sensing device are similar to those used in the dual channel electro-optical sensing devices described in the aforementioned U.S. Pat. No. 6,330,464. In accordance with the present invention, however, the sensing device 100 is configured to define a hermetically sealed chamber 108, preferably holding an analyte-containing fluid 110 in direct contact with the indicator membrane 103B of the reference channel. If the fluid 110 in the chamber 108 contains the same type of analyte contained in the external environment, such an arrangement ensures that the response over time of the reference channel to changes in the radiation source, the temperature of the external environment, and photo-oxidation of the membrane are essentially the same as or similar to the response of the signal channel thereto. At the same time, the hermetic seal isolates the reference channel from changes in the concentration of the analyte in the external environment so that environmental factors other than analyte concentration can be canceled out by using the ratio of the signal and reference channel outputs as described above.

In the illustrated embodiment, the signal and reference channels of the sensing device 100 are incorporated in a chip-like package with leads 112 extending therefrom for providing power, signals, etc., to and/or from the device. The illustrated package includes a device substrate 114 in the form of a rectangular printed circuit board, two rows of leads 112 disposed along opposite edges of the substrate, and a housing 116 mounted on the substrate between the rows of leads. In a preferred embodiment, the substrate 114 is formed of an alumina ceramic. Discrete components can be electrically connected to the substrate, for example using commonly available solder paste or conductive epoxy such as, for example, ABLEBOND 84 from Ablestick Electronic Materials.

Housing 116 includes a generally rectangular top wall 118 and two side walls 120A and 120B depending downwardly from opposite edges of the top wall. Bottom edges of the sidewalls 120A and 120B are configured to mount on a top surface of substrate 114 so as to maintain the top wall 118 in vertically spaced relation to the substrate. The housing 116 can be formed of any material suitable for use in the environment of interest but is preferably formed of a relatively rigid plastic or metal material to improve accuracy by maintaining the top wall and substrate in vertically spaced, parallel planes. The entire region R between the housing 116 and the substrate 114 can be empty but preferably contains a waveguide material such as, for example, Epoxy Technologies 301™ which has good optical characteristics, although other suitable materials can be used. The complete optical path (i.e., between the radiation source, the indicator membranes, and the photosensitive elements) is preferably refractive index matched so that maximum light capture with minimal internal reflection losses occur.

First and second openings 122A and 122B are formed through the top wall 118 of the housing 116 at spaced locations to communicate with the indicator membranes 103A and 103B. The openings 122A and 122B are preferably arranged symmetrically on the top wall 118 so that the indicator membranes 103A and 103B are subjected to similar conditions. In the illustrated embodiment, for example, the openings 122A and 122B are both arranged along a longitudinal axis of the housing 116 equidistant from opposite edges of the top wall 118. The openings 122A and 122B are shown as identical circular holes that are somewhat smaller than the indicator elements 102A and 102B; however, the shape and/or size of the openings can be varied to accommodate different types of elements.

Indicator elements 102A and 102B are disposed within the housing 116 adjacent the openings 122A and 122B formed in the top wall 118 thereof. The indicator elements 102A and 102B shown in this embodiment include rectangular substrates 105A and 105B, respectively, that are somewhat larger than the openings 122A and 122B so that peripheral portions of the substrates can be affixed to an interior surface of the housing 116 around the openings to form a hermetic seal. As mentioned above, indicator elements 102A and 102B also include indicator molecules having one or more optical characteristics that are affected by the local presence of an analyte. The indicator molecules are preferably part of a membrane or layer 103A and 103B formed on a central portion of a respective substrate 105A and 105B in alignment with openings 122A and 122B. The membrane substrates 105A and 105B are preferably formed of the same material and with the same thickness so that the indicator elements exhibit similar thermal properties. In an exemplary embodiment, the membrane substrates are formed of an optically transparent material such as borosilicate glass and the membrane includes an inorganic polymer support matrix termed sol-gels or ormosils, into which the indicator molecule is immobilized or entrapped. These materials and techniques are well known (See, e.g.: McDonagh et al., "Tailoring of Sol-Gel Films for Optical Sensing of Oxygen in Gas and Aqueous Phase", Analytical Chemistry, Vol. 70, No. 1, Jan. 1, 1998, pp. 45–50; Lev. O. "Organically Modified Sol-Gel Sensors", Analytical Chemistry, Vol. 67, No. 1, Jan. 1, 1995; MacCraith et al., "Development of a LED-based Fibre Optic Oxygen Sensor Using a Sol-Gel-Derived Coating", SPIE, Vol. 2293, pp. 110–120 ('94); Shahriari et al., "Ormosil Thin Films for Chemical Sensing Platforms", SPIE, Vol. 3105, pp. 50–51 ('97); Krihak et al., "Fiber Optic Oxygen Sensors Based on the Sol-Gel Coating Technique", SPIE, Vol. 2836, pp. 105–115 ('96), the entire disclosures of which are each incorporated herein by reference). These types of materials can be applied to the appropriate indicator element substrate by a number of techniques that are well known in the art, such as dipping, swabbing, squeegeeing, silk screening, pad printing, vapor deposition, ink-jet printing, etc. In an alternative embodiment, one or both of the indicator elements can be formed without a dedicated substrate, for example by mounting an indicator membrane directly on a cover, an encapsulant, or some other part of the device.

A preferred indicator molecule for sensing oxygen is tris(4,7-diphenyl-1,10-phenanthroline) ruthenium (II) perchlorate molecule, discussed on column 1, lines 16–19, of U.S. Pat. No. 5,517,313. It is contemplated that the membranes can include a variety of other materials as set forth in the aforementioned U.S. Pat. No. 6,330,464, incorporated herein by reference.

The radiation source 106 is mounted on the substrate 114 at an appropriate location to excite the indicator molecules on each of the indicator elements 102A and 102B. To maintain commonality between the channels, the radiation source 106 is preferably located equidistant from each of the indicator elements 102A and 102B. Any suitable radiation source can be used; however, a light-emitting diode (LED) is preferred. The wavelength of the radiation emitted by the source is dependent upon the type of indicator molecule employed. For example, in the case of the ruthenium molecule referenced above, it is preferred that the radiation source emit light in the blue or ultra-violet bands, for example at 460 nm. While the radiation source 106 is shown centrally located between the photosensitive elements 104A and 104B and the indicator elements 102A and 102B, the radiation source may be otherwise located, as long as adequate excitation is provided to the signal and reference channel membranes.

Photosensitive elements 104A and 104B are mounted on the device substrate 114 on opposite sides of the radiation source 106 in general alignment with indicator elements 102A and 102B, respectively. Silicon photo-diodes, such as for example part no. 150-20-002 from Advanced Photonics, Inc., are preferably provided as the photosensitive elements, and are preferably flip chip mounted using ball bonds and conductive epoxy. Optical filters 124A and 124B are preferably provided for each of the photosensitive elements. In an exemplary embodiment, each optical filter is formed using a high-pass filter epoxy, such as LP-595 filter resin available from CVI Laser Corporation, with, for example, a 600 nm cutoff corresponding to the ruthenium molecule fluorescent emission. In another exemplary embodiment, each optical filter is fabricated from commercially available filter sheet stock. The optical filters preferably separate fluorescent emission from the indicator membranes from the excitation energy of the radiation source. In an alternative embodiment, each optical filter can be formed using a bandpass filter that rejects wavelengths outside a predetermined range. Bandpass filters are commercially available from numerous vendors and allow the device to operate in environments with ambient light.

A cover 126B is mounted over the reference channel opening 122B in spaced relation to the indicator element 102B to define the hermetically-sealed chamber 108 that isolates the reference channel from changes in the concentration of the analyte in the external environment while ensuring that the reference channel responds like the signal channel to other environment changes external to the sensing device (e.g., temperature) as well as changes in operations intrinsic to the sensing device (e.g., photodegradation and fluctuations in the power source). In the illustrated embodiment, the reference channel cover 126B includes a cylindrical plug 128B configured to fit within the opening 122B and a circular flange 130B extending radially outward from an upper or top end of the plug. As best seen in FIG. 7, the plug 128B fits snugly in the opening 122B and extends part way through the thickness of the housing wall 118 such that a gap is maintained between a bottom of the plug and the indicator membrane. The circular flange 130B extending radially outward from the top of the plug 128B defines a lower annular contact surface adapted to contact an upper or outer surface of the housing 116 completely around the circumference of the opening 122B so that an hermetic seal can be formed that will prevent migration of analyte-containing fluids from the external environment into the chamber. The reference channel cover 126B can be formed of any suitable material but is preferably formed of an analyte-impermeable material having good thermal conductivity so that the fluid in the chamber will experience temperature changes similar to the fluid in the external environment. It can also be advantageous for the material to have high reflectivity. Examples of suitable materials for the cover include, but are not limited to, metals such as brass, aluminum, and steel. It is also contemplated that insulating and semi-insulating materials such as plastics and ceramics can be used. When the external environment includes background radiation coinciding with the wavelength of interest, it may be desirable for the cover to be formed of a transparent material so that such background radiation can be canceled. The cover 126B can be affixed to the housing 116 using any technique capable of producing an hermetic seal, but is preferably bonded using an adhesive suitable for the particular housing and cover materials.

It will be appreciated that the presence of the sealed chamber 108 above the reference indicator element 102B can result in the channels being unbalanced due to the enhanced thermal insulation provided by the fluid-filled gap and the additional light reflected by the cover 126B. To compensate for these effects, the sensing device 100 is shown with an optional signal channel cover 126A mounted over the signal channel opening 122A. The signal channel cover 126A is identical to the reference channel cover 126B described above but is modified to permit direct contact between the signal channel indicator element 102A and fluid in the external environment. In the illustrated embodiment, the cover 126A is rendered porous by forming a bore 132 through the cover. The bore 132 is preferably much smaller than the size of the opening 122A (e.g., less than about 50% of the opening area) to mimic the reflectance and thermal properties of the reference channel cover 126B. While a single bore 132 is shown, it will be appreciated that any number of channels or bores may be formed in the signal channel cover. Alternatively, or in addition to bores, grooves may be formed across the annular contact surface in communication with flutes or openings formed in the plug to provide fluid communication between the indicator element 102A of the signal channel and the external environment.

While the sensing device 100 can be fabricated in a variety of ways by those skilled in the art based on this disclosure, one exemplary method of making the device shown in FIGS. 6 and 7 is as follows. The circuit substrate 114 can be custom manufactured but is preferably of a type (e.g., alumina ceramic or fiberglass) that can be obtained commercially from a large number of vendors. Circuits including components such as amplifiers, filters and inductors can be formed on the substrate 114 in any conventional manner, such as by bonding the components directly onto the substrate, for example using commonly available solder paste or conductive epoxy such as ABLEBOND 84 from Ablestick Electronic Materials. The circuit components can then be wire bonded, if necessary, to complete the circuit connections. Silicon photo-diodes, such as, for example, part no. 150-20-002 from Advanced Photonics, Inc., can be used as the photosensitive elements 104A and 104B, and are preferably flip chip mounted onto the substrate using ball bonds and conductive epoxy. Filters 124A and 124B can be formed using optical filter material, such as, for example, LP-595 from CVI Laser Corporation or commercially available sheet stock. The filters 124A and 124B can be formed separately and bonded to the photosensitive elements 104A and 104B, or the filters can be formed directly on the photosensitive elements. As mentioned above, the radiation source 106 is preferably mounted on the substrate 114 between the photosensitive elements 104A and 104B in symmetrical relation to the indicator elements 102A and 102B.

The indicator elements 102A and 102B and covers 126A and 126B can be attached to the housing 116 in any suitable manner but are preferably bonded using adhesives suitable for the respective materials. A preferred method of fabricating the housing assembly includes bonding the indicator elements 102A and 102B to an interior surface of the housing 116 such that the indicator molecules contained by the membranes face outwardly of the housing through the respective openings 122A and 122B in the housing and bonding the covers 126A and 126B to an exterior surface of the housing over the openings. Preferably, the step of bonding or otherwise sealing the reference cover 126B is performed in an environment having properties appropriate for the environment in which measurements are to be taken. Alternatively, the chamber can be filled with a fluid that is different from the external medium (so long as, in the case of a gaseous analyte, the partial pressure of the analyte in the chamber fluid is within the range of expected partial pressures of the analyte in the external medium). For example, it has been found that a device with an air-filled reference chamber can be used effectively to detect dissolved oxygen over a wide range of partial pressures in a liquid medium such as water or blood.

The housing 116 can be attached to the substrate 114 in any conventional manner but is preferably bonded thereto using an adhesive. An optically transparent encapsulant 134 can be injected into the space R between the housing 116 and the substrate 114 to serve as a waveguide and, together with the covers 126A and 126B, provide environmental protection for the circuitry. If the housing 116 is formed of a relatively flexible material, the encapsulant 134 can also help maintain spatial alignment of optical components such as the membranes and the photosensitive elements.

An exemplary operation of the electro-optical sensing device 100 shown in FIGS. 6 and 7 is as follows. The sensing device 100 is positioned in an environment or medium of interest to measure the concentration of an analyte in the medium. In an exemplary embodiment, the environment is air within a respiratory circuit and the analyte is oxygen. When a measurement is desired, power is supplied to the radiation source 106 to cause the source to emit radiation in the sensing device. In the illustrated embodiment, power is drawn from an external source via the leads 112. It will be appreciated, however, that power can be provided from an internal power source such as a battery or from an external source via an induction circuit formed in the sensing device as described in the aforementioned U.S. Pat. No. 6,330,464, incorporated herein by reference.

The radiation emitted by the radiation source 106 propagates within the sensing device (as shown generally by arrows in FIG. 7) and reaches both the signal membrane 103A and the reference membrane 103B. Indicator molecules contained by these respective membranes are excited by the radiation and, in turn, radiate light back into the sensing device (as also shown generally by arrows). The light radiated by the indicator membranes 103A and 103B is modulated (i.e., attenuated or enhanced) by the local presence of an analyte. For example, it is known that the orange-red fluorescence of the complex tris(4,7-diphenyl-1, 10-phenanthroline) ruthenium(II) perchlorate is quenched by the local presence of oxygen. As mentioned above, the sealed chamber 108 in the sensing device holds a fluid 110 with a suitable concentration of analyte in direct contact with the reference membrane 103B whereas the signal channel is exposed to the external environment or medium. Thus, modulation of the light radiated from the signal membrane 103A should be due in part to changes in the amount of analyte present in the external environment whereas modulation of the light radiated from the reference membrane 103B should be due entirely to other factors such as temperature, photo-oxidation, and fluctuations in the power source. Since the covers 126A and 126B mounted over each of the openings 122A and 122B in the housing 116 are substantially similar in structure, these other factors should similarly affect both channels.

It should be understood that, in the case of gaseous analyte, the above sensing device actually measures the partial pressure of the analyte, the behavior of which is widely understood. Although the sensing device measures partial pressure, this is readily converted to concentration, if desired, using known techniques.

Light from each of the indicator elements 102A and 102B propagates through the sensing device to a corresponding photosensitive element 104A or 104B via a filter 124A or 124B. Filters 124A and 124B are configured to allow the light emitted by the indicator molecules to reach the photosensitive elements 104A and 104B while filtering out scattered light from the radiation source (and, depending upon circumstances, ambient light that may interfere with the signal). Photosensitive elements 104A and 104B generate electrical outputs in response to the light received from the indicator elements 102A and 102B, respectively. These outputs can be transmitted directly to an external device via the leads 112 for processing and/or processed internally using circuits formed in the sensing device 100 before transmission. An output proportional only to analyte concentration in the external environment can be obtained by taking the ratio of the signal and reference channel outputs since factors other than analyte concentration will tend to affect both the signal and reference channels in equal measure and, thus, be canceled.

Figure 8:
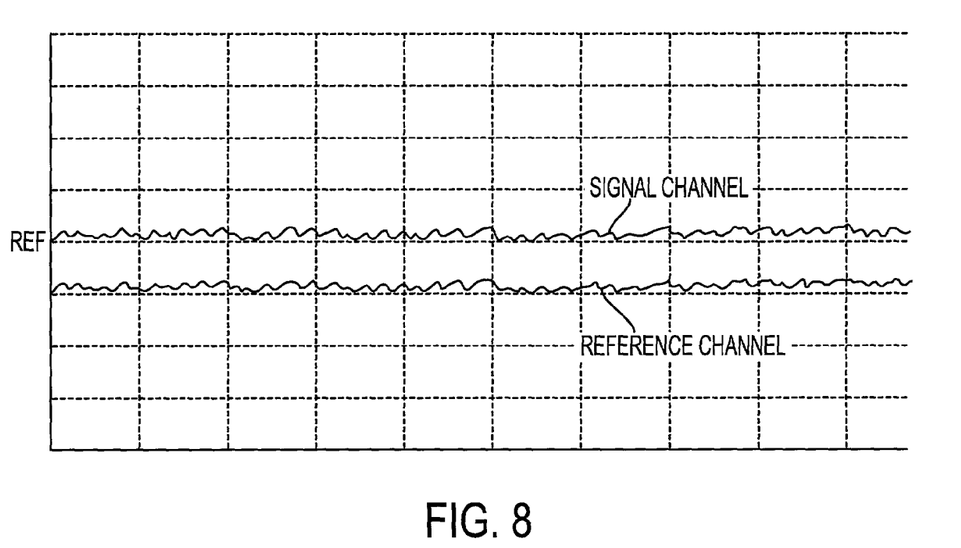
FIG. 8 is a graph demonstrating the effects of temperature and photodegradation over time for the signal and reference channels of the electro-optical sensing device shown in FIGS. 6 and 7.

FIG. 8 shows actual test data of signal and reference channel outputs for a sensing device 100 as shown in FIGS. 6 and 7 having a reference chamber filled with air. The test was conducted under the same conditions described above in connection with the sensing device 10 as shown in FIG. 4. As can be seen, the reference and signal channel outputs A and B for device 100 respond in like manner over time to environmental and systemic changes so that the ratio of the outputs C will always be a flat line absent changes in analyte concentration in the external medium. The ratio can thus be used to provide an output proportional only to analyte change.

It is contemplated that the sensing device 100 illustrated in FIGS. 6 and 7 can be modified in a variety of ways. For example, the size and/or shape of the packaging can be modified to suit various applications. The packaging can include leads as shown or any other means for establishing connections with external devices including, without limitation, wireless connections established using radio-frequency (RF) transmitters and receivers. The device can be powered by an internal source such as a battery or by an external source via leads, induction, or some other mechanism.

The configuration and arrangement of the various features of the device can also be varied. For example, the openings in the top wall of the housing can be circular as shown, rectangular, or have any other configuration. The openings can be arranged anywhere in the housing but are preferably symmetrically arranged relative to the radiation source to ensure commonality between the signal and reference channels. Similarly, the indicator elements can be rectangular as shown, circular, or have any other configuration. The indicator membranes can be carried on a substrate or mounted on other parts of the device such as the covers. When a separate membrane substrate is used it can be a plate-like member as shown, a waveguide material filling the space between the internal components of the device, or have any other suitable configuration. In addition, the indicator elements can be disposed above or below the top wall of the housing, within an opening formed in the top wall of the housing, or in pockets formed in the encapsulant. Also, a baffle or partition can be positioned between the indicator elements to inhibit "cross-talk" of light radiated from the signal and reference channel membranes. Such a baffle would preferably be impervious to radiation that could affect the photosensitive elements.

The housing can have any configuration to support the various components of the device. For example, the housing can include one or more walls that extend from the substrate to support indicator elements in spaced relation to the photosensitive elements. Preferably, the space between the excitation source, indicator elements, and photosensitive elements is filled with an encapsulant formed of a waveguide material. If an encapsulant is used, the encapsulant can serve as the housing to support the operational components without the use of walls.

While the use of fluorescent indicator molecules to measure oxygen is described above, it should be understood that other types of indicator molecules and combinations thereof can be used depending on the particular analyte of interest. For example, light-absorbing indicator molecules, such as those described in U.S. Pat. No. 5,512,246, the disclosure of which is incorporated herein by reference, can be used to measure polyhydroxyl compounds such as sugars, including glucose. In another example, indicator molecules, such as those described in U.S. Pat. No. 6,344,360, U.S. patent application Ser. No. 10/029,184, filed Dec. 28, 2001, U.S. patent application Ser. No. 10/028,831, filed Dec. 28, 2001 and U.S. Provisional Patent Application Serial No. 60/363,885, filed Mar. 14, 2002, the disclosures of which are incorporated herein by reference, can be used to measure vicinal diols, polyhydroxyl compounds such as sugars, including glucose. In some circumstances it may be possible to utilize fluorescent indicator molecules in one of the membranes while using light-absorbing indicator molecules in the other of the membranes. In most cases, however, the signal and reference membranes will both use like indicator molecules, such as described herein.

Preferably, both the reference channel and the signal channel include a cover mounted over a corresponding opening formed in the sensing device housing. The signal channel cover is preferably similar to the reference channel cover but can be of significantly different design so long as adequate commonality is achieved. The signal channel can also be operated without a cover if desired. The reference and signal channel covers can include planar members that sit flush against a surface of the housing, convex members that define a space adjacent a surface of the housing, plugs that fit within openings in the housing, or any combination of the foregoing. The covers can also be formed as an integral part of the housing.

In another embodiment, the device can be provided with multiple radiation sources (e.g., LEDs) disposed within the same housing or in different housings mounted on the same substrate. In yet another embodiment, the device can be modified so as to include a plurality of signal membranes (e.g., to measure the same or different analytes) and/or a plurality of reference membranes (e.g., to measure the same or different optical properties). In addition, while the embodiment shown herein has only two channels (i.e., a signal channel and a reference channel), other embodiments could contain multiple signal channels and/or multiple reference channels.

The ability of this device to measure oxygen levels from inhaled and exhaled respiratory gases has significant medical utility. For example, the device can be utilized in conjunction with flow or volume measuring devices to determine the uptake and release of respiratory gases, enabling the measurement of critical medical parameters such as metabolic rate (calorie expenditure), indirect cardiac output based on the Fick principle (first described in theory by Adolph Fick in 1870), pulmonary function, and onset of shock. Many of these medical diagnostic determinations require the measurement of the partial pressure respiratory gases at the very end of an exhalation (known as end-tidal pO2 or end-tidal pCO2 levels). While the illustrated example is preferably used for the measurement of oxygen, the sensing device can easily be modified to measure other analytes, for example by use of different indicator membranes.

It will be appreciated that the sensing device of the present invention can be used in any environment having one or more analytes that can be sensed. For example, the sensing device can be employed in mediums made up of solid, liquid or gaseous mediums or combinations thereof. The reference chamber is preferably filled with a medium corresponding to the external medium but can be filled with any type of medium. For example, tests have shown that a sensing device with a sealed reference chamber filled with air can be used to measure oxygen concentration in a liquid environment. In some cases, it may be desirable to create a vacuum in the chamber.

While the sensing device has been described above as measuring intensity, it is also possible to detect the presence and concentration of an analyte by measuring fluorescence decay time with the device.

While the invention has been described in detail above, the invention is not intended to be limited to the specific embodiments as described. It is evident that those skilled in the art may now make numerous uses and modifications of and departures from the specific embodiments described herein without departing from the inventive concepts.

We claim:

1. An electro-optical sensing device for detecting the presence of an analyte in a medium, said sensing device comprising:
   a. a radiation source that emits radiation;
   b. a first and a second photosensitive elements configured to receive radiation and output an electrical signal in response thereto;
   c. a first and a second indicator elements positioned to receive radiation from the radiation source and to transmit radiation to said first and second photosensitive elements, said first and second indicator elements each containing indicator molecules with an optical characteristic responsive to the presence of an analyte; and
   d. a hermetically-sealed chamber covering said second indicator element so as to render said second indicator element insensitive to the presence of the analyte in a medium external to the device,
   wherein said first indicator element is in fluid communication with said external medium and said second indicator element is not in fluid communication with said external medium, and
   wherein said hermetically-sealed chamber contains an analyte-containing fluid in contact with said second indicator element.

2. The sensing device of claim 1, further comprising a housing, wherein said first and second indicator elements, said first and second photosensitive elements, and said radiation source are mounted in said housing.

3. The sensing device of claim 1, further comprising an analyte-impermeable cover mounted on the housing which defines at least a portion of the chamber covering the second indicator element.

4. The sensing device of clam 1, further comprising an analyte-permeable cover mounted on the housing over the first indicator element.

5. The sensing device of claim 4, wherein said analyte-permeable cover includes a bore formed therethrough to provide fluid communication between the first indicator element and the external medium.

6. The sensing device of claim 1, wherein said first indicator element and said first photosensitive comprise a signal channel, and wherein said second indicator element and said second photosensitive element comprise a reference channel.

7. The sensing device of claim 1, wherein said analyte-containing fluid is a liquid.

8. The sensing device of claim 1, wherein said analyte-containing fluid is a gas.

9. The sensing device of claim 1, wherein an analyte in said analyte-containing fluid is the same type of analyte to be detected in the external medium.

10. The sensing device of claim 1, wherein an analyte in said analyte-containing fluid is a different type of analyte than the analyte to be detected in the external medium.

11. The sensing device of claim 1, wherein said indicator molecule has an optical characteristic responsive to the presence of oxygen.

12. The sensing device of claim 11, wherein said indicator molecule is tris(4,7-diphenyl-1,10-phenanthroline)ruthenium(II) perchlorate.

13. A method for detecting an analyte of interest in a medium, said method comprising:
   a. providing an electro-optical sensing device containing a first and a second indicator elements each containing indicator molecules having an optical characteristic responsive to the presence of an analyte and positioned to receive excitation radiation from a radiation source and to transmit resultant radiation to a pair of photosensitive elements, and wherein said first indicator element is covered by a cover having at least one bore therethrough and said second indicator element is covered by an analyte-impermeable, hermetically-sealed chamber that renders the second indicator element insensitive to the presence of the analyte in the medium external to the device;
   b. introducing a medium to contact said first indicator element through the bore in said cover;
   c. activating said radiation source to emit radiation to said first and second indicator elements, and optically detecting an optical response of said first and second indicator elements; and
   d. evaluating said response to determine the presence or concentration of at least one analyte of interest in the sample, wherein said response detected from said second indicator element is used as a reference to cancel variables that affect both said first and second indicator elements.

* * * * *